US008754074B2

(12) United States Patent
Nicolas et al.

(10) Patent No.: US 8,754,074 B2
(45) Date of Patent: Jun. 17, 2014

(54) VINYL QUINUCLIDINE USEFUL AS A SYNTHESIS INTERMEDIATE IN THE PREPARATION OF (R)-MEQUITAZINE

(75) Inventors: Marc Nicolas, Gaillac (FR); Laurent Larquetoux, Toulouse (FR); Sébastien Leroux, Baune (FR); Eric Doris, Orsay (FR)

(73) Assignees: Pierre Fabre Medicament, Boulogne-Billancourt (FR); Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/822,649

(22) PCT Filed: Jan. 10, 2012

(86) PCT No.: PCT/EP2012/050305
§ 371 (c)(1),
(2), (4) Date: Mar. 13, 2013

(87) PCT Pub. No.: WO2012/095418
PCT Pub. Date: Jul. 19, 2012

(65) Prior Publication Data
US 2013/0296553 A1    Nov. 7, 2013

(30) Foreign Application Priority Data
Jan. 10, 2011    (FR) ..................... 11 50186

(51) Int. Cl.
*A61K 31/54*    (2006.01)
*A61K 31/44*    (2006.01)
*A01N 43/90*    (2006.01)
*C07D 453/02*    (2006.01)
*C07D 295/00*    (2006.01)
*C07D 417/00*    (2006.01)

(52) U.S. Cl.
USPC .................. 514/225.2; 514/222.8; 514/227.8; 514/305; 546/133; 544/42

(58) Field of Classification Search
USPC ....................................... 514/225.2; 546/133
See application file for complete search history.

(56) References Cited

FOREIGN PATENT DOCUMENTS

EP          0 089 860 A1    9/1983
WO    WO 93/03029 A1    2/1993

OTHER PUBLICATIONS

Guminski et al., "An Efficient Synthesis of Mequitazine", Organic Preparations and Procedures International, vol. 31, No. 3, 1999, pp. 319-323.
Lukes et al., "Über Einige β-Substituierte Derivate Des Chinuclidins IV. Darstellung Eines Optisch Aktiven 3-Vinylchinuclidins Aus Cinchonin.", Collection of Czechoslovak Chemical Communications, vol. 18, 1953, pp. 829-834 and English Summary thereof.

*Primary Examiner* — John Mabry
*Assistant Examiner* — Daniel Carcanague
(74) *Attorney, Agent, or Firm* — Birch, Stewart, Kolasch & Birch, LLP

(57) ABSTRACT

The present invention relates to the use of the vinyl quinuclidine enantiomer (R) of the following formula 2 as a synthesis intermediate in the preparation of (R)-mequitazine.

9 Claims, No Drawings

VINYL QUINUCLIDINE USEFUL AS A SYNTHESIS INTERMEDIATE IN THE PREPARATION OF (R)-MEQUITAZINE

The present invention relates to the optically pure vinyl quinuclidine of the following formula 2 as a synthesis intermediate in the preparation of the (R) enantiomer, dextrorotary, of the mequitazine of the following formula 1a:

Scheme 1

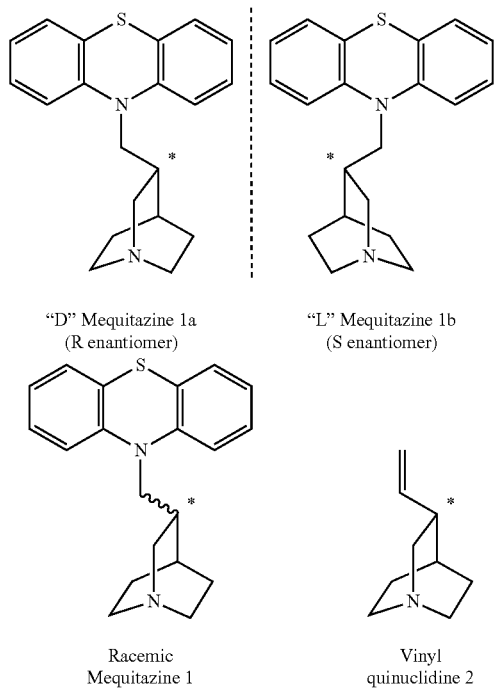

"D" Mequitazine 1a (R enantiomer)

"L" Mequitazine 1b (S enantiomer)

Racemic Mequitazine 1

Vinyl quinuclidine 2

Mequitazine 1 is an active ingredient developed by the Pierre Fabre laboratories and commercialised in the racemic version thereof (mixture of 2 enantiomers 1a and 1b, Scheme 1) under the name of Primalan®. This medicine is used as an antihistaminic for the treatment for example of urticaria, hay fever or certain allergies. Its preparation in the racemic form and in the levorotary form thereof 1b has been described in the patents FR 2 522 660 and EP 0 089 860. The drawback of the protocol for synthesising mequitazine in an optically active form (1a or 1b) is that it involves a step of resolution of the racemic, via the formation of a complex with tartaric acid. This resolution involves the loss of 50% at least of product (loss of the undesired enantiomer) and leads to an optically enriched compound.

The inventors of the present invention have thus developed a novel method of synthesising mequitazine 1a using vinyl quinuclidine 2 as synthesis intermediate thus making it possible to avoid a step of resolution of a racemic mixture.

The present invention thus relates to the (R) enantiomer of vinyl quinuclidine of the following formula 2:

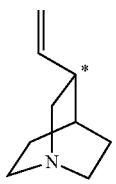

2 and pharmaceutically acceptable salts thereof.

This compound 2 will have particularly an enantiomeric excess (ee) greater than 95%, particularly greater than 96%, in particular greater than 97%, more particularly greater than 98%, and advantageously greater than 99%.

"Enantiomeric excess" is taken to mean, according to the present invention, the difference between the molar fraction of the majority enantiomer ((R) enantiomer in the case of vinyl quinuclidine) and the molar fraction of the minority enantiomer ((S) enantiomer in the case of vinyl quinuclidine).

"Molar fraction" is taken to mean, according to the present invention, the ratio between the quantity in moles of the enantiomer in question and the quantity in moles of the two enantiomers.

"Pharmaceutically acceptable" is taken to mean, according to the present invention, everything that is useful in the preparation of a pharmaceutical composition, which is generally non-toxic and which is acceptable for veterinary and/or human pharmaceutical use.

"Pharmaceutically acceptable salts" is taken to mean, according to the present invention, salts that are pharmaceutically acceptable, as defined above, and which have the desired pharmacological activity of the parent compound. Such salts include:

(1) acid addition salts formed with inorganic acids such as hydrochloric acid, sulphuric acid, nitric acid, bromic acid, phosphoric acid and similar or formed with organic acids such as ascorbic acid, benzoic acid, aspartic acid, oxalic acid, benzene sulphonic acid, tartaric acid, glutamic acid, lactic acid, maleic acid, succinic acid, fumaric acid, citric acid, malic acid, mandelic acid, methane sulphonic acid, pantothenic acid, para-toluene sulphonic acid, acetic acid, gluconic acid, ethane sulphonic acid, propionic acid, salicylic acid, trifluoroacetic acid and similar; advantageously it is trifluoroacetic acid; or (2) the salts formed when the proton acid present in the parent compound is either replaced by a metal ion, for example an alkaline metal ion, an alkaline earth metal ion or an aluminium ion; or is coordinated with an organic or inorganic base. Acceptable organic bases include diethanolamine, ethanolamine, N-methylglucamine, triethanolamine, tromethamine and similar. Acceptable inorganic bases include aluminium hydroxide, calcium hydroxide, potassium hydroxide, sodium carbonate and sodium hydroxide.

Advantageously the pharmaceutically acceptable salt is an acid addition salt, advantageously formed with trifluoroacetic acid.

The present invention moreover proposes a method of synthesising the compound 2. The approach implemented is based on the use, as starting material, of a family of molecules extracted from quinquina bark: the alkaloids of *Cinchona*. These alkaloids have a structural homology that is going to be put to profit for the construction of the backbone of (R)-mequitazine.

The alkaloids of *Cinchona* 3 are characterised by a quinuclidine nucleus (homologous to that of mequitazine) substituted by two hanging groups: a side chain of "benzylic alcohol" type and a vinylic group, both of defined stereochemistry (Scheme 2). The strategy implemented profitably makes use of the stereochemistry of the vinylic group for the creation of the stereogenic centre of the (R) enantiomer of mequitazine. It is necessary beforehand to fragment the side chain of the *Cinchona* backbone in order to lead to the optically pure vinyl quinuclidine nucleus 2 which is the key intermediate of the synthesis. The vinyl quinuclidine intermediate 2 may then serve as precursor for the synthesis of mequitazine via oxidative cleavage of the double bond, reduction of the aldehyde obtained, activation of the alcohol obtained and coupling with phenothiazine.

Scheme 2

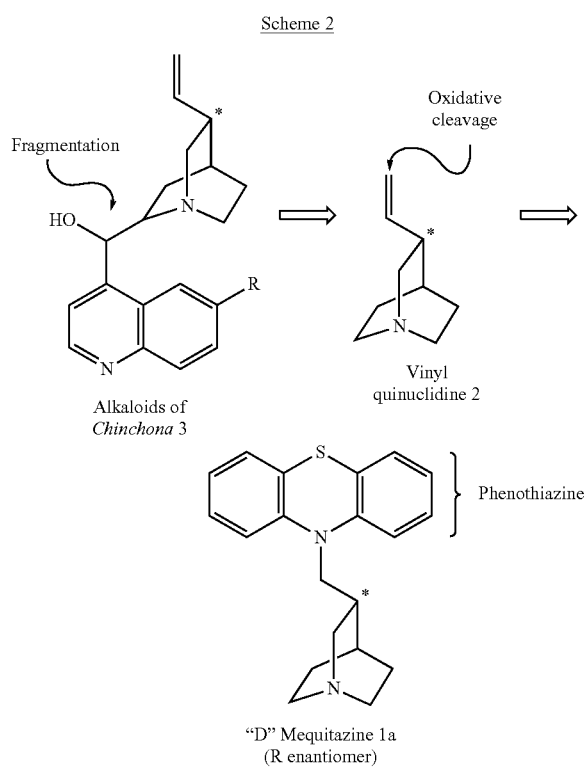

The advantages of this approach via the alkaloids of Cinchona are:
- No "random" creation of the stereogenic centre born by the quinuclidine nucleus because it is already present on the starting alkaloid with an absolute optical purity (this centre will be preserved throughout the synthesis),
- No loss of half of the raw material used due to resolution, and
- An abundant and cheap starting material derived from biomass.

The family of alkaloids of Cinchona includes different members that differ by the nature and the stereochemistry of the side chain (e.g.: quinine, cinchonidine, quinidine, cinchonine) but in which the stereochemistry of the "vinyl" group is constant. The synthesis method developed functions equally well from the different members of the family of alkaloids of Cinchona.

The present invention thus also relates to a method of synthesising the (R) enantiomer of vinyl quinuclidine from an alkaloid of Cinchona of the following formula 3:

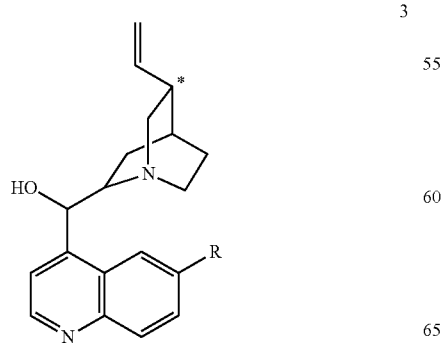

for which the carbon atom marked with a star is of (R) configuration and R represents a hydrogen atom, a $(C_1-C_6)$alkoxy group such as methoxy, or a R4-OH group in which R4 represents a $(C_1-C_6)$alkyl group.

"$(C_1-C_6)$alkyl group" is taken to mean, according to the present invention, a saturated hydrocarbon chain, linear or branched, comprising 1 to 6, preferably 1 to 4, carbon atoms. It may be a methyl, ethyl, isopropyl, n-propyl, n-butyl, sec-butyl, isobutyl, tert-butyl, pentyl or hexyl group.

"$(C_1-C_6)$alkoxy", is taken to mean, according to the present invention, a saturated hydrocarbon chain, linear or branched, comprising 1 to 6, preferably 1 to 4, carbon atoms, bonded to the rest of the molecule through the intermediary of an oxygen atom. It can be a methoxy, ethoxy, n-propoxy, isopropoxy, n-butoxy, sec-butoxy, isobutoxy, tert-butoxy, pentoxy or hexoxy group. It may in particular be a methoxy or tert-butoxy group.

The alkaloid of Cinchona of formula 3 could be selected more particularly from quinine, cinchonidine, quinidine and cinchonine, and particularly will be quinine.

The method of synthesising the (R) enantiomer of vinyl quinuclidine will include more particularly the following successive steps:

(i) oxidation of the alcohol function born by the alkaloid of Cinchona of formula 3 as defined previously to give the ketone of the following formula 4:

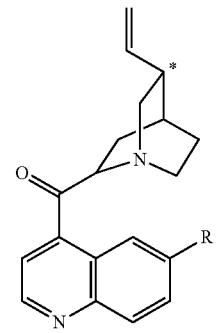

for which the carbon atom marked with a star is of (R) configuration and R is as defined previously, (ii) auto-oxidation of the ketone of formula 4 obtained at the preceding step (i) to give the ester of the following formula 5:

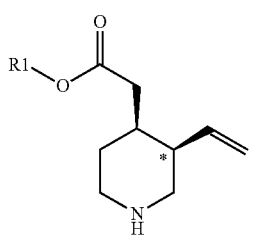

for which the carbon atom marked with a star is of (R) configuration and R1 represents a $(C_1-C_6)$alkyl group such as tert-butyl, (iii) reduction of the ester of formula 5 obtained at the preceding step (ii) to give an alcohol of the following formula 6:

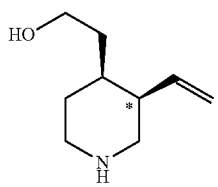

6 for which the carbon atom marked with a star is of (R) configuration, and (iv) cyclisation of the alcohol of formula 6 obtained at the preceding step (iii) to give the (R) enantiomer of vinyl quinuclidine of formula 2 as defined previously.

Step (i):

Step (i) could be carried out more particularly in the presence of dimethyl sulphoxide (DMSO) and oxalyl chloride, in other words in Swern oxidation conditions.

The reaction will be carried out particularly at a temperature comprised between −60 and −80° C., particularly at around −78° C. Dichloromethane could be used as solvent.

Step (ii):

Step (ii) could be carried out in the presence of oxygen (the oxygen being particularly made to bubble in the reaction medium) and a base of formula R1-O-M such as t-BuOK, R1 being as defined previously and representing particularly a tert-butyl group and M representing an alkaline metal such as sodium or potassium, and particularly potassium.

The reaction could be carried out in the presence of the alcohol of formula R1-OH corresponding to the base, such as tert-butanol. Tetrahydrofuran could be used as solvent.

Step (iii):

Step (iii) could be carried out in the presence of a hydride such as lithium aluminium hydride (LAB). Tetrahydrofuran could be used as solvent.

Step (iv):

The step of cyclisation (iv) will particularly include the following two successive steps:

(iv-1) activation of the OH function of the alcohol of formula 6 as defined previously to give the compound of the following formula 7:

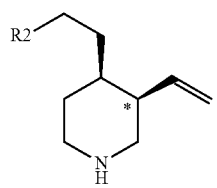

for which the carbon atom marked with a star is of (R) configuration and R2 representing a leaving group such as a chlorine atom, and (iv-2) cyclisation of the compound of formula 7 in the presence of a base to give the (R) enantiomer of vinyl quinuclidine of formula 2 as defined previously.

"Leaving group" is taken to mean, according to the present invention, a chemical group that may be easily displaced by a nucleophile during a nucleophilic substitution reaction, the nucleophile being more particularly an amine, and particularly a secondary amine. Such a leaving group may be more particularly a halogen atom such as a chlorine atom, a mesylate ($CH_3$—$S(O_2)O$—), triflate ($CF_3$—$S(O)_2O$—) or a tosylate (p-Me-$C_6H_4$—$S(O)_2O$—).

Step (iv-1) could be carried out in the presence of $SOCl_2$ when R2=Cl. Dichloromethane could be used as solvent.

Step (iv-2) could be carried out in the presence of $K_2CO_3$ as base. Acetonitrile could be used as solvent. A catalytic quantity of sodium iodide may also be added. The compound 2 thereby obtained could be separated from the reaction medium by methods well known to those skilled in the art, such as for example by extraction, evaporation of the solvent or by precipitation and filtration. It could moreover be purified if necessary by techniques well known to those skilled in the art, such as recrystallization, distillation, chromatography on silica gel column or high performance liquid chromatography (HPLC).

The present invention thus relates to the use of the (R) enantiomer of vinyl quinuclidine 2 as synthesis intermediate in the preparation of the (R) enantiomer of mequitazine.

The present invention also relates to a method of synthesising the (R) enantiomer of mequitazine from the (R) enantiomer of vinyl quinuclidine 2.

This method could include more particularly the following successive steps:

(a) oxidative cleavage of the double bond of the (R) enantiomer of the vinyl quinuclidine of formula 2 as defined previously to give the aldehyde of the following formula 8:

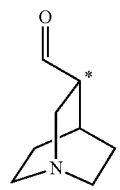

for which the carbon atom marked with a star is of (R) configuration, (b) reduction of the aldehyde of formula 8 obtained at the preceding step (a) to give the alcohol of the following formula 9:

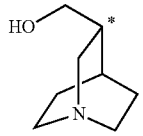

for which the carbon atom marked with a star is of (R) configuration, (c) activation of the OH function of the alcohol of formula 9 obtained at the preceding step (b) to give a compound of the following formula 10:

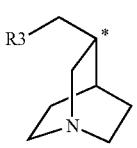

for which the carbon atom marked with a star is of (R) configuration and R3 represents a leaving group such as a mesylate (OMs or CH$_3$—S(O$_2$)O—), and (d) coupling of the compound of formula 10 obtained at the preceding step (c) with phenothiazine to give the (R) enantiomer of mequitazine.

Step (a):

Step (a) could be carried out by ozonolysis, in other words in the presence of O$_3$, in which methanol may be used as solvent. This reaction could be carried out from an acid addition salt of the (R) enantiomer of the vinyl quinuclidine of formula 2 as defined previously, the acid being able to be more particularly trifluoroacetic acid. The advantage of the use of such a salt is that it protects the basic nitrogen from oxidising conditions.

Step (b):

Step (b) could be carried out in the presence of a hydride such as NaBH$_4$.

Step (c):

Step (c) could be carried out in the presence of mesyl chloride (MsCl), also called methanesulphonyl chloride, and a base such as pyridine, when R3=OMs. Chloroform could be used as solvent.

Step (d):

Step (d) is carried out in the presence of a base such as potassium tert-butoxylate. Tetrahydrofuran could be used as solvent.

The mequitazine 1a thereby obtained could have an enantiomeric excess (ee) greater than 95%, particularly greater than 96%, in particular greater than 97%, more particularly greater than 98%, and advantageously greater than 99%.

EXAMPLES

The following abbreviations have been used:
TLC Thin Layer Chromatography
DMSO Dimethyl sulphoxide
ESI Electrospray ionisation
LAH Lithium aluminium hydride (LiAlH$_4$)
Ms Mesyl
NMP N-Methyl-2-pyrrolidone
Pyr Pyridine
Rf Front ratio
Rfx Reflux
NMR Nuclear Magnetic Resonance
MS Mass Spectrometry
TFA Trifluoroacetic acid
THF Tetrahydrofuran
TOF Time of flight By way of example, the quinine 3i has been transformed into vinyl quinuclidine 2 according to the reaction scheme below (Scheme 3).

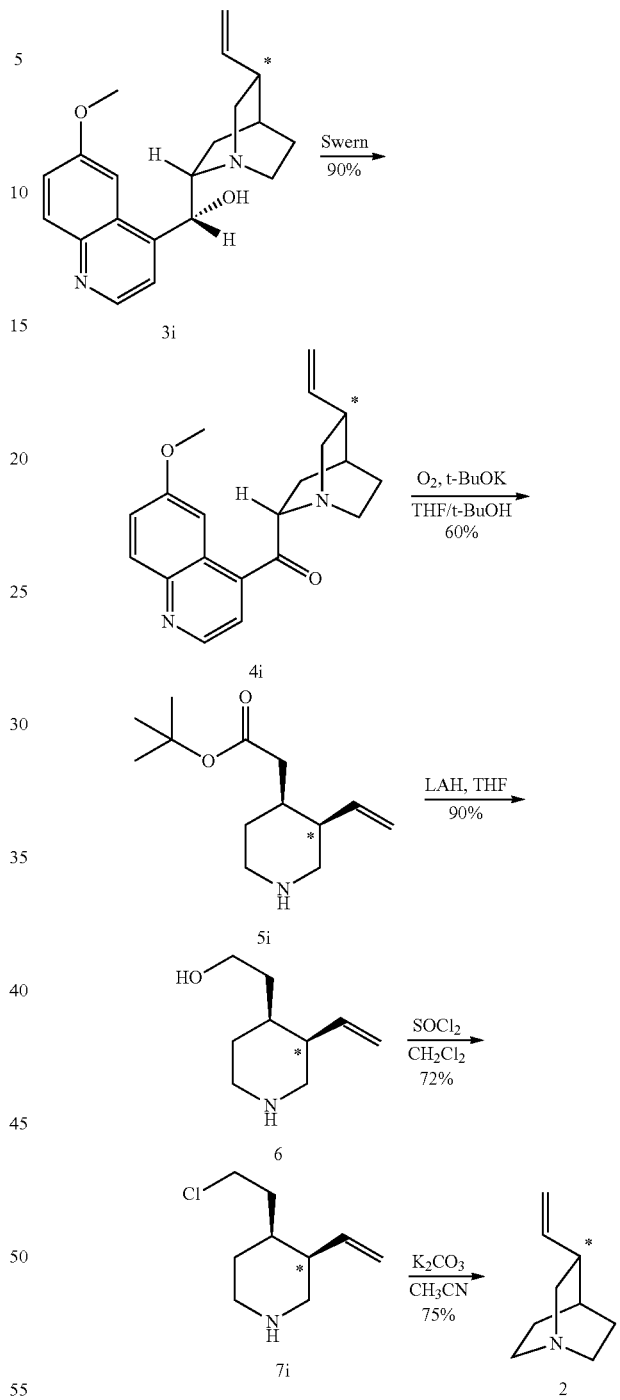

Scheme 3

Synthesis of the ketone 4i

In a 250 mL round bottomed flask, dried beforehand, anhydrous DMSO (1.6 mL, 22.5 mmol, 5.2 eq) is introduced drop by drop into a solution of oxalyl chloride (770 µL, 9.1 mmol, 2.1 eq) in 20 mL of anhydrous CH$_2$Cl$_2$ at −78° C. under nitrogen atmosphere. The medium is left stirring for 20 minutes at this temperature then a solution of quinine 3i (1.4 g, 4.32 mmol, 1 eq) in 20 mL of CH$_2$Cl$_2$ is added drop by drop to the medium over a period of 15 minutes. After one hour of stirring at −78° C., anhydrous triethylamine (5.35 mL, 38.4 mmol, 8.9 eq) is added drop by drop, the medium is left 15 minutes at −78° C. then 1 h at ambient temperature. The reaction is stopped by addition of 25 mL of a saturated NaCl solution and 10 mL of water. The medium is extracted with 3×25 mL of $CH_2Cl_2$. The combined organic phases are dried on $Na_2SO_4$, filtered, then evaporated under vacuum. The crude is purified by chromatography on silica gel (eluent: $CH_2Cl_2$/MeOH/$NH_4OH$ 95/4.5/0.5) to lead to a fraction of quininone 4i which solidifies with difficulty. The fraction is taken up in several mL of water to precipitate the quininone which is filtered then dried overnight under vacuum on $P_2O_5$ to lead to 1.25 g (90%) of 4i in the form of a light yellow solid.

$C_{20}H_{22}N_2O_2$, M=322.40 g·mol$^{-1}$. Rf: 0.3 ($CH_2Cl_2$/MeOH/$NH_4OH$ 90/9/1).

$^1$H NMR (400 MHz, CDCl$_3$): 8.84 (1H, d, J=4.4 Hz), 8.03 (1H, d, J=9.2 Hz), 7.65-7.64 (2H, m), 7.40 (1H, dd, J=9.2 Hz, J=2.8 Hz), 5.97 (1H, ddd, J=17.2 Hz, J=10.3 Hz, J=7.4 Hz), 5.05 (1H, ddd, J=10.3 Hz, J=1.6 Hz, J=1.2 Hz), 5.03 (1H, ddd, J=17.2 Hz, J=1.6 Hz, J=1.3 Hz), 4.19 (1H, t, J=9.0 Hz), 3.93 (3H, s), 3.16-3.08 (1H, m), 2.95-2.84 (2H, m), 2.62 (1H, ddd, J=14.0 Hz, J=7.5 Hz, J=2.1 Hz), 2.40-2.33 (1H, m), 2.26 (1H, ddd, J=13.5 Hz, J=7.5 Hz, J=1.0 Hz), 1.89 (1H, m), 1.73-1.65 (2H, m), 1.58-1.50 (1H, m).

$^{13}$C NMR (100 MHz, CDCl$_3$): 203.0; 159.0; 146.9; 145.5; 141.4; 140.2; 131.4; 125.7; 122.6; 119.9; 1148; 102.6; 62.9; 55.4; 49.6; 48.7; 27.6; 27.3; 22.0; 21.6.

MS (ESI+ TOF): 323 [M+H]$^+$ (100).

Synthesis of the t-butylic ester 5i

In a 10 mL round bottomed flask, dried beforehand, anhydrous t-BuOH (0.4 mL) is added to a solution of freshly sublimated t-BuOK (174 mg, 1.55 mmol, 2.5 eq) in 1 mL of anhydrous THF. The solution is saturated by bubbling oxygen for 10 minutes at 0° C. then left under $O_2$ atmosphere. A solution of 4i (200 mg, 0.62 mmol, 1 eq) in 1 mL of anhydrous THF is added drop by drop. The medium turns to dark orange. After 30 minutes at 0° C., a TLC shows that the quininone 4i has been entirely consumed, the medium turning yellow. The stirring is stopped then 5 mL of $Et_2O$ are added leading to the precipitation of a yellow solid, which is removed by filtration. The solid is rinsed with 5 mL of $Et_2O$, then the mother liquors are concentrated under vacuum. Precipitation in ether is repeated 4 times and the filtrate is finally evaporated to lead to 86 mg (60%) of 5i in the form of viscous yellow oil.

$C_{13}H_{23}NO_2$, M=225.33 g·mol$^{-1}$.

$^1$H NMR (400 MHz, CDCl$_3$): 6.06 (1H, ddd, J=17.0 Hz, J=10.5 Hz, J=9.0 Hz), 5.12 (1H, ddd, J=10.5 Hz, J=1.6 Hz, J=1.2 Hz), 5.05 (1H, ddd, J=17.0 Hz, J=1.6 Hz, J=1.2 Hz), 3.04 (1H, ddd, J=12.5 Hz, J=45 Hz, J=3.0 Hz), 2.94 (1H, dd, J=12.4 Hz, J=3.2 Hz), 2.87 (1H, dd, J=12.4 Hz, J 20=3.2 Hz), 2.70 (1H, ddd, J=12.5 Hz, J=10.9 Hz, J=3.2 Hz), 2.29 (1H, m), 2.20-2.05 (3H, m), 1.49-1.36 (2H, m), 1.44 (9H, s).

$^{13}$C NMR (100 MHz, CDCl$_3$): 172.3; 137.1; 116.6; 79.8; 51.2; 46.1; 43.0; 38.9; 35.7; 28.9; 28.1.

MS (ESI+ TOF): 226 [M+H]$^+$ (100).

$[\alpha]^{20}_D$=+45.4° (c=0.099; CHCl$_3$).

Synthesis of the Alcohol 6

In a 10 mL round bottomed flask, dried beforehand, LiAlH$_4$ (LAH) (33.7 mg, 0.89 mmol, 4 eq) is added by portions to a solution of 5i (50 mg, 0.22 mmol, 1 eq) in 1.5 mL of anhydrous THF at 0° C. The reaction is stopped after 4 h of stirring at ambient temperature under nitrogen atmosphere.

1.5 mL of 1M caustic soda and 2 mL of water are added successively to the medium which is left stirring for 20 minutes. The alumina formed is filtered on celite which is thoroughly rinsed with THF then with a 3:1 THF/MeOH mixture. The filtrate is evaporated under vacuum, concentrated to lead to 30.8 mg (90%) of 6 in the form of yellow oil which is directly used in the following step.

$C_9H_{17}NO$, M=155.24 g·mol$^{-1}$, Rf: 0.1 ($CH_2Cl_2$/MeOH/$NH_4OH$ 90/9/1).

$^1$H NMR (400 MHz, CDCl$_3$): 6.12 (1H, ddd, J=17.1 Hz, J=10.2 Hz, J=9.0 Hz), 5.26 (1H, ddd, J=5 10.2 Hz, J=1.6 Hz, J=0.9 Hz), 5.14 (1H, ddd, J=17.1 Hz, J=1.6 Hz, J=1.1 Hz), 3.66 (2H, J=6.4 Hz), 3.07 (1H, ddd, J=12.4 Hz, J=46 Hz, J=2.9 Hz), 2.97 (1H, dd, J=12.4 Hz, J=3.2 Hz), 2.88 (1H, dd, J=12.4 Hz, J=3.2 Hz), 2.68 (1H, ddd, J=12.4 Hz, J=10.5 Hz, J=3.6 Hz), 2.25 (1H, m), 1.82-1.74 (1H, m), 1.63-1.39 (4H, m).

$^{13}$C NMR (100 MHz, CDCl$_3$): 137.6; 116.4; 60.4; 51.9; 46.3; 43.1; 36.3; 35.0; 29.1.

Synthesis of the Chloride 7i

In a 25 mL round bottomed flask, dried beforehand, thionyl chloride (94 μL, 1.28 mmol, 2 eq) is added drop by drop to a solution of 6 (100 mg, 0.64 mmol, 1 eq) in 5 mL of anhydrous $CH_2Cl_2$ under nitrogen atmosphere and at 0° C. The medium is then heated to reflux for 2 h. The medium is cooled to 0° C., neutralised with 6 mL of an aqueous saturated $K_2CO_3$ solution then extracted with 4×10 mL of $CH_2Cl_2$. The combined organic phases are dried on $Na_2SO_4$ filtered, then evaporated under vacuum to lead to 7i in the form of a brown oil which is used directly in the following step.

$C_9H_{16}ClN$, M=173.68 g·mol$^{-1}$, Rf: 0.27 ($CH_2Cl_2$/MeOH/$NH_4OH$ 90/9/1).

$^1$H NMR (400 MHz, CDCl$_3$): 6.09 (1H, ddd, J=17.0 Hz, J=10.3 Hz, J=8.9 Hz), 5.16-5.07 (2H, 20 m), 3.56 (2H, J=6.8 Hz), 3.10 (1H, ddd, J=12.2 Hz, J=5.0 Hz, J=2.8 Hz), 3.00 (1H, dd, J=12.4 Hz, J=2.8 Hz), 2.90 (1H, dd, J=12.4 Hz, J=2.8 Hz), 2.71 (1H, ddd, J=12.2 Hz, J=10.5 Hz, J=3.3 Hz), 2.27 (1H, m), 1.87 (1H, m), 1.79-1.61 (2H, m), 1.58-1.42 (2H, m).

$^{13}$C NMR (100 MHz, CDCl$_3$): 137.1; 115.8; 51.8; 46.4; 45.2; 42.4; 34.2; 33.8; 28.9.

Synthesis of Vinyl Quinuclidine 2

In a 25 mL round bottomed flask, dried beforehand, potassium carbonate (120 mg, 0.87 mmol, 1.5 eq) is added in one go to a solution of 7i (100 mg, 0.58 mmol, 1 eq) in 10 mL of anhydrous acetonitrile. A spatula tip of sodium iodide is introduced before heating the medium to reflux for 2 h. The reaction is stopped then the acetonitrile is evaporated under vacuum. The medium is taken up in 10 mL of water, extracted with 4×10 mL of chloroform. The combined organic phases are dried on $Na_2SO_4$, filtered, then evaporated under vacuum. The crude is purified by chromatography on silica gel (eluent: $CH_2Cl_2$/MeOH/$NH_4OH$ 90/9/1) to lead to 58 mg (75%) of 2 in the form of a yellow oil.

$C_9H_{15}N$, M=137.22 g·mol$^{-1}$, Rf: 0.20 ($CH_2Cl_2$/MeOH/$NH_4OH$ 90/9/1).

$^1$H NMR (400 MHz, CDCl$_3$): 5.89 (1H, ddd, J=16.8 Hz, J=9.9 Hz, J=8.2 Hz), 5.07-4.99 (2H, m), 3.04 (1H, ddd, J=13.2 Hz, J=10.0 Hz, J=2.0 Hz), 2.89-2.71 (4H, m), 2.71 (1H, ddd, J=13.2 Hz, J=6.4 Hz, J=2.0 Hz), 2.35-2.26 (1H, m), 1.77-1.54 (4H, m), 1.43-1.33 (1H, m).

$^{13}$C NMR (100 MHz, CDCl$_3$): 141.2; 114.3; 51.2; 47.5; 46.8; 40.0; 27.4; 26.6; 21.2.

MS (ESI+ TOF): 138 [M+H]+ (100).

$[\alpha]_D^{20}$=+54.7° (c=0.098; CHCl$_3$).

Vinyl quinuclidine 2 was used for the synthesis of mequitazine of (R), dextrorotary, stereochemistry, (Scheme 4).

Scheme 4

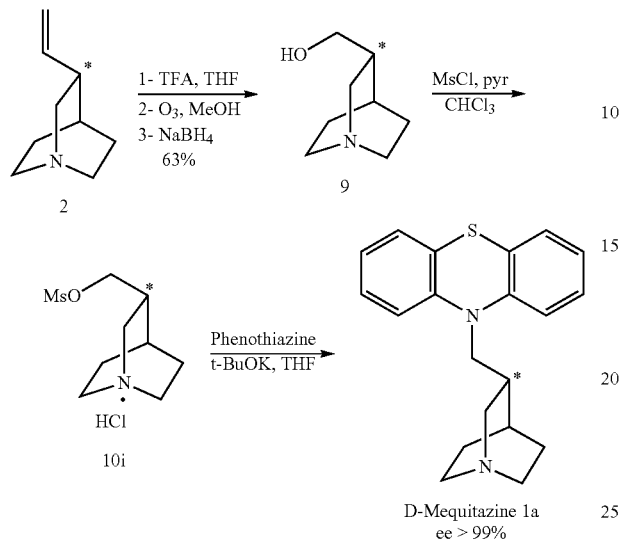

Synthesis of Quinuclidine-Methanol 9

In a 10 mL round bottomed flask, TFA (30 μL, 0.38 mmol, 1.1 eq) is added to a solution of vinyl quinuclidine 2 (48 mg, 0.35 mmol, 1 eq) in THF (1 mL). The medium is left under stirring for 10 minutes, then the THF is evaporated under vacuum. The vinyl quinuclidine salt is taken up in 2 mL of MeOH and the temperature of the medium is cooled to −78° C. Ozone is bubbled in the solution up to saturation (appearance of a violet colour after 5 min). The excess of ozone is then eliminated by bubbling nitrogen in the medium for 10 minutes. Solid NaBH$_4$ (106 mg, 2.8 mmol, 8 eq) is then introduced in one go then the medium is progressively brought to ambient temperature. After 16 h, the reaction is stopped by addition of 4 mL of an aqueous saturated K$_2$CO$_3$ solution. The aqueous phase is extracted with 4×5 mL of ethyl acetate. The combined organic phases are dried on Na$_2$SO$_4$, filtered, then evaporated under vacuum. The crude reaction mixture (31 mg, 63%) is used directly in the following step (yellow oil).

C$_8$H$_{15}$NO, M=141.21 g·mol$^{-1}$, R$_f$: 0.05 (CH$_2$Cl$_2$/MeOH/NH$_4$OH 90/9/1).

$^1$H NMR (400 MHz, CDCl$_3$): 3.51 (2H, d, J=8.4 Hz), 2.97 (1H, dd, J=13.4 Hz, J=9.9 Hz), 2.84-5 2.70 (4H, m), 2.30 (1H, ddd, J=13.4 Hz, J=6.5 Hz, J=2.0 Hz), 1.85-1.76 (2H, m), 1.70-1.56 (2H, m), 1.56-1.48 (1H, m), 1.42-1.33 (1H, m).

$^{13}$C NMR (100 MHz, CDCl$_3$): 64.4; 51.6; 47.6; 47.2; 38.4; 27.7; 21.9; 21.3.

MS (ESI+ TOF): 142 [M+H] (100).

$[\alpha]_D^{20}$=+50.2° (c=0.1; CHCl$_3$).

Synthesis of the Mesylate 10i

In a 5 mL round bottomed flask, a solution of the alcohol 9 (22 mg, 0.16 mmol, 1 eq) in 1 mL of CHCl$_3$ is cooled to 0° C. Pyridine (15 μL, 0.19 mmol, 1.2 eq) then methanesulphonyl chloride (15 μL, 0.19 mmol, 1.25 eq) are added drop by drop. At the end of the addition, the medium is brought to ambient temperature. After 4 hours stirring, the precipitate obtained is filtered, rinsed 3 times with acetone then dried under vacuum. The mesylate 10i (24.2 mg, 61%) is obtained in the hydrochloride form thereof (pale yellow solid).

C$_9$H$_{18}$ClNO$_3$S, M=255.76 g·mol$^{-1}$, Re: 0.25 (CH$_2$Cl$_2$/MeOH/NH$_4$OH 80/18/2) (KMnO$_4$ developer). The spectral data ($^1$H and $^{13}$C NMR) are in agreement with those of the mesylate described by Imbert et al. (Guminski, Y., Fabre, V., Lesimple, P., Imbert, T. *Organic Preparations and Procedures International* 1999, 31, 319-323).

Synthesis of Dextrorotary (R)-Mequitazine 1a

In a 5 mL round bottomed flask, a solution of t-BuOK (13.2 mg, 0.12 mmol, 3 eq) in 0.5 mL of NMP is added to the reaction mixture containing mesylate hydrochloride 10i (10 mg, 39 μmol, 1 eq), phenothiazine (15.6 mg, 78 μmol, 2 eq) in 1 mL of anhydrous THF heated to 60° C. The medium turns dark red after 2 h 30 at this temperature. The reaction is brought to ambient temperature, hydrolysed and extracted with 3×3 mL of Et$_2$O. The organic phases are combined then washed with water. The organic phase is extracted twice with an aqueous solution at pH 2. The aqueous phase is then washed with Et$_2$O and concentrated. The solid is taken up in 1.5 mL H$_2$O/Et$_2$O (1/0.5) in an ice bath. The precipitate is filtered, rinsed with Et$_2$O and taken up in 4 mL of saturated K$_2$CO$_3$. The aqueous phase is extracted with 3×3 mL of CHCl$_3$. The organic phases are dried on Na$_2$SO$_4$, filtered then concentrated under vacuum. The mequitazine 1a (9.1 mg, 72%) is obtained in the form of a white solid.

C$_{20}$H$_{22}$N$_2$S, M=322.47 g·mol$^{-1}$, R$_f$: 0.50 (CH$_2$Cl$_2$/MeOH/NH$_4$OH 80/18/2) (UV developer).

The spectral data (NMR) of the mequitazine are in agreement with the authentic product. The absolute stereochemistry of the (R)-mequitazine 1a was determined by measurement of the specific rotary power ($[\alpha]_D^{20}$=+43.4 (c=0.098, EtOH)) and the enantiomeric excess by chiral HPLC:

column OD 256×46 mm flow rate: 1 mL·min$^{-1}$

Eluent: Hexane/EtOH 97: 3+0.5% HNEt$_2$, t$_r$ (S)-mequitazine (control): 10.3 min, t$_r$ (R)-mequitazine: 12.2 min. The enantiomeric excess of (R)-mequitazine is greater than 99%.

The invention claimed is:

1. A method of synthesising the (R) enantiomer of mequitazine from the (R) enantiomer of vinyl quinuclidine of the following formula 2:

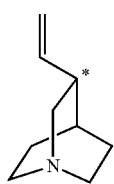

comprising the following successive steps:

(a) oxidative cleavage of the double bond of the (R) enantiomer of the vinyl quinuclidine of formula 2 to give the aldehyde of the following formula 8:

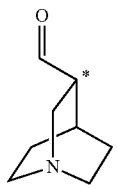

8 for which the carbon atom marked with a star is of (R) configuration, (b) reduction of the aldehyde of formula 8 obtained at the preceding step (a) to give the alcohol of the following formula 9:

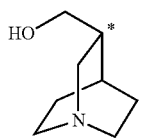

9 for which the carbon atom marked with a star is of (R) configuration, (c) activation of the OH function of the alcohol of formula 9 obtained at the preceding step (b) to give a compound of the following formula 10:

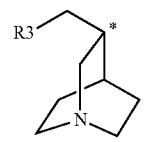

10 for which the carbon atom marked with a star is of (R) configuration and R3 represents a leaving group, selected from a halogen atom, a mesylate ($CH_3$—$S(O_2)$O—), a triflate ($CF_3$—$S(O)_7O$—) and a tosylate (p-Me—$C_6H_4$—$S(O)_2O$—), and (d) coupling of the compound of formula 10 obtained at the preceding step (c) with phenothiazine to give the (R) enantiomer of mequitazine.

2. The method according to claim 1, wherein step (a) is carried out by ozonolysis.

3. The method according to claim 2, wherein step (a) is carried out on an acid addition salt of the (R) enantiomer of the vinyl quinuclidine of formula 2 as defined in claim 1.

4. The method according to claim 1, wherein step (b) is carried out in the presence of a hydride which is $NaBH_4$.

5. The method according to claim 1, wherein R3 represents a mesylate ($CH_3$—$S(O_2)O$—).

6. The method according to claim 5, wherein step (c) is carried out in the presence of mesyl chloride (MsCl) and a base.

7. The method according to claim 6, wherein the base is pyridine.

8. The method according to claim 1, wherein step (d) is carried out in the presence of a base.

9. The method according to claim 8, wherein the base is potassium tert-butoxylate.

* * * * *

UNITED STATES PATENT AND TRADEMARK OFFICE
CERTIFICATE OF CORRECTION

PATENT NO.        : 8,754,074 B2
APPLICATION NO.   : 13/822649
DATED             : June 17, 2014
INVENTOR(S)       : Marc Nicolas et al.

It is certified that error appears in the above-identified patent and that said Letters Patent is hereby corrected as shown below:

IN THE SPECIFICATION:

Column 1, line 43, change "racemic form" to --racemic form 1--.

Column 5, line 36, change "(LAB)" to --(LAH)--.

Column 11, line 59, change "142 [M+H] (100)" to --142 $[M+H]^+$ (100)--.

Column 12, line 9, change "Re: 0.25" to --$R_f$: 0.25--.

IN THE CLAIMS:

Claim 1, at column 14, line 12, change "a triflate ($CF_3$—$S(O)_7O$—)" to --a triflate ($CF_3$-$S(O)_2O$—)--.

Signed and Sealed this
Thirteenth Day of January, 2015

Michelle K. Lee
*Deputy Director of the United States Patent and Trademark Office*